US007731938B2

(12) United States Patent
Karl et al.

(10) Patent No.: US 7,731,938 B2
(45) Date of Patent: Jun. 8, 2010

(54) CYFRA 21-1 AS A MARKER FOR COLORECTAL CANCER

(75) Inventors: Johann Karl, Peissenberg (DE); Herbert Andres, Penzberg (DE); Veit Peter Grunert, Munich (DE); Wolfgang Rollinger, Polling (DE); Werner Zolg, Weilheim-Unterhausen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 67 days.

(21) Appl. No.: 11/764,913

(22) Filed: Jun. 19, 2007

(65) Prior Publication Data
US 2008/0020414 A1 Jan. 24, 2008

Related U.S. Application Data

(63) Continuation of application No. PCT/EP2005/013867, filed on Dec. 22, 2005.

(30) Foreign Application Priority Data
Dec. 23, 2004 (EP) .................................. 04030619

(51) Int. Cl.
*A61K 49/00* (2006.01)
(52) U.S. Cl. ....................................................... 424/9.1
(58) Field of Classification Search ........................ None
See application file for complete search history.

(56) References Cited

U.S. PATENT DOCUMENTS

2004/0038225 A1  2/2004  Markowitz

FOREIGN PATENT DOCUMENTS

| EP | 1439393 A2 | 7/2004 |
| WO | 2004/057336 A2 | 7/2004 |
| WO | 2004/104593 A1 | 12/2004 |

OTHER PUBLICATIONS

Yeh et al, "Monitoring Cytokeratin Fragment 10 (CYFRA 21-1) Serum Levels for Early Prediction of Recurrence of Adenocarcinoma and Squamous Cell Carcinom in the Lung after Surgical Resection," (Lung), 2002, vol. 180, pp. 273-279.*
Kashihara et al, "Intrahepatic cholangiocarcinoma with increased serum CYFRA 21-1 level," (J. Gastroenterol) 1998, vol. 33, pp. 447-453.*
Bernick et al, "Neuroendocrine Carcinomas of the Colon and Rectum," (Dis of the Colon and Rectum), 2004, vol. 47, pp. 163-169.*
Molina et al. "Study of a new tumor marker, CYFRA 21-1, in malignant and nonmalignant diseases", Tumor Biol., 1994, 15:318-325.*
Ahlquist, D., "Fecal Occult Blood Testing for Colorectal Cancer," Colorectal Neoplasia, Part II, 26;1 (Mar. 1997) 41/55.
Bodenmuller, H. et al., "Lung Cancer-Associated Keratin 19 Fragments: Development and Biochemical Characterisation of the New Serum Assay Enzymun-Test CYFRA 21-1," The International Journal of Biological Markers, 9;2 (1994) 75-81.

Duffy, M. et al., "Clinical utility of biochemical markers in colorectal cancer: European Group on Tumour Markers (EGTM) guidelines," European Journal of Cancer, 39 (2003) 718-727.
Ebert, W. et al., "Cytokeratin 19 Fragment CYFRA 21-1 Compared with Carcinoembryonic Antigen, Squamous Cell Carcinoma Antigen and Neuron-Specific Enolase in Lung Cancer," Eur. J. Clin. Chem. Clin. Biochem, 32 (1994) 189-199.
Hoffmann, D. et al., "The Prognostic Value of CEA, CA242, CA19-9, CA72-4, CYFRA 21-1 and S100 in Colorectal Cancer," Tumor Biol, 24 (2003) 49-Abstract P-14 CEA.
Kojima, O. et al., "Tumor Marker, Serological Detection of Cancer," Rinsho Byori. Jap. Clin. Pathol. 34 (2004) 337-339.
Lamerz, R., Clinical Laboratory Diagnostics: Use and Assessment of Clinical Laboratory Results, First Edition, TH-Books Verlagsgesellschaft mbH, Frankfurt/Main, Germany.
Martell, R.E. et al., "OVX1 and CEA in Patients with Colon Carcinoma, Colon Polyps and Benign Colon Disorders," The International Journal of Biological Markers, 13;3 (1998) 145-149.
Matsumoto, H., Journal of Japan Society of Coloproctology, 55 (2002) 136-144.
Matsumoto, H., Database Biosci, Info. Servc. Philadelphia (2002)—Database accession No. PREV200200296087-XP002329221.
Miyashita, T. et al., Database Biosci, Info. Servc. Philadelphia (2002)—Database accession No. PREV200000195119-XP002329220.
Miyashita, T. et al., Journal of Japan Society of Coloproctology,53 (2000)76-82.
Nakata, B. et al., "Serum CYFRA 21-1 (cytokeratin-19 fragments) is a useful tumour marker for detecting disease relapse and assessing treatment efficacy in breast cancer," British Journal of Cancer, 91 (2004) 873-878.
Qiang, Z. et a., "Diagnostics Value of Multi-Tumor Markers Protein Biochip Detective System for Digestive Tract Cancer," Zhongguo Zhongliu Linchaung, 31 (2004) 337-339.
Sakahara, H. et al., Kakuigaku, 30 (1993) 1475-1479.
Sturgeon, C., "Practice Guidelines for Tumor Marker Use in the Clinic," Clinical Chemistry, 48:8 (2002) 1151-1159.
Van Der Gaast, A. et al., "Evaluation of a New Tumour Marker in Patients with Non-Small-Cell Lung Cancer: Cyfra 21.1," Br. J. Cancer, 69 (1994) 525-528.
Vaughn, C. et al., "Ferritin, A Potential Marker for Cancer of the Colon," Proc. Am. Assoc. Cancer Res. Annual Meeting, 30 (19989) 26-Abstract No. 101.
Yokoyama, T. et a., "Methylation of ASC/TMS1, a proapoptotic gene responsible for activating procaspase-1, in human colorectal cancer," Cancer Letters, 202 (2003) 101-108.
Zweig, M. et al., "Receiver-Operating Characteristic (ROC) Plots: A fundamental Evaluation Tool in Clinical Medicine," Clin. Chem., 39;4 (1993) 561-577.

* cited by examiner

*Primary Examiner*—Karen Cochrane Carlson
*Assistant Examiner*—Bin Shen
(74) *Attorney, Agent, or Firm*—Marilyn Amick (57) ABSTRACT

The present invention relates to the assessment of colorectal cancer. It discloses the use of the CYFRA 21-1 assay in the assessment of colorectal cancer. It also relates to a method for assessing colorectal cancer in vitro using a liquid sample, derived from an individual by measuring CYFRA 21-1 in said sample. Measurement of CYFRA 21-1 can, e.g., be used in the early detection or in the follow-up of patients with colorectal cancer.

3 Claims, 5 Drawing Sheets

CYFRA 21-1 AS A MARKER FOR COLORECTAL CANCER

RELATED APPLICATIONS

This application is a continuation of PCT application PCT/EP2005/013867 filed Dec. 22, 2005 and claims priority to European application EP 04030619.3 filed Dec. 23, 2004.

FIELD OF THE INVENTION

The present invention relates to a method aiding in the assessment of colorectal cancer using cytokeratin 19 (CYFRA 21-1). In particular, it relates to a method for assessing colorectal cancer in a liquid sample from an individual by measuring CYFRA 21-1 in said sample. Measurement of CYFRA 21-1 can, e.g., be used in the early detection of colorectal cancer or in the surveillance of patients who undergo therapy, e.g. surgery.

BACKGROUND

The present invention relates to a method aiding in the assessment of colorectal cancer (CRC). It discloses the use of the CYFRA 21-1 as a marker of colorectal cancer. Furthermore, it especially relates to a method for assessing colorectal cancer from a liquid sample, derived from an individual by measuring CYFRA 21-1 in said sample. Measurement of CYFRA 21-1 can, e.g., be used in the early detection of colorectal cancer or in the surveillance of patients who undergo therapy, e.g. surgery.

Cancer remains a major public health challenge despite progress in detection and therapy. Amongst the various types of cancer, colorectal cancer is one of the most frequent cancers in the Western world.

Colorectal cancer most frequently progresses from adenomas (polyps) to malignant carcinomas. The different stages of CRC used to be classified according to Dukes' stages A to D.

The staging of cancer in the classification of the disease in terms of extent, progression, and severity. It groups cancer patients so that generalizations can be made about prognosis and the choice of therapy.

Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), edition, 1997 (Sobin, L. H., and Fleming, I. D., TNM 80 (1997) 1803-4).

What is especially important is, that early diagnosis of CRC translates to a much better prognosis. Most malignant tumors of the colorectum appear to arise from benign tumors, i.e. from adenoma. Therefore, best prognosis have those patients diagnosed at the adenoma stage. Patients diagnosed as early as in stage $T_{is}$, N0, M0 or T1-3; N0; M0, if treated properly have a more than 90% chance of survival 5 years after diagnosis as compared to a 5-years survival rate of only 10% for patients diagnosed when distant metastases are already present.

In the sense of the present invention early diagnosis of CRC refers to a diagnosis at a pre-malignant state (adenoma) or at a tumor stage where no metastases at all (neither proximal nor distal), i.e., adenoma, $T_{is}$, N0, M0 or T1-4; N0; M0 are present. $T_{is}$ denotes carcinoma in situ.

It is further preferred, that CRC is diagnosed when it has not yet fully grown through the bowel wall and thus neither the visceral peritoneum is perforated nor other organs or structures are invaded, i.e., that diagnosis is made at stage $T_{is}$, N0, M0 or T1-3; N0; M0 (=$T_{is}$-3; N0; M0).

The earlier cancer can be detected/diagnosed, the better is the overall survival rate. This is especially true for CRC. The prognosis in advanced stages of tumor is poor. More than one third of the patients will die from progressive disease within five years after diagnosis, corresponding to a survival rate of about 40% for five years. Current treatment is only curing a fraction of the patients and clearly has the best effect on those patients diagnosed in an early stage of disease.

With regard to CRC as a public health problem, it is essential that more effective screening and preventative measures for colorectal cancer be developed.

The earliest detection procedures available at present for colorectal cancer involve using tests for fecal occult blood or endoscopic procedures. However, significant tumor size must typically exist before fecal blood is detected. The sensitivity of the guaiac-based fecal occult blood tests is ~26%, which means 74% of patients with malignant lesions will remain undetected (Ahlquist, D. A., Gastroenterol. Clin. North Am, 26 (1997) 41-55). The visualization of precancerous and cancerous lesions represents the best approach to early detection, but colonoscopy is invasive with significant costs, risks, and complications (Silvis, S. E., et al., JAMA 235 (1976) 928-930; Geenen, J. E., et al., Am. J. Dig. Dis. 20 (1975) 231-235; Anderson, W. F., et al., J. Natl. Cancer Institute 94 (2002) 1126-1133).

In order to be of clinical utility a new diagnostic marker as a single marker should be at least as good as the best single marker known in the art. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

The clinical utility of biochemical markers in colorectal cancer has recently been reviewed by the European Group on Tumor Markers (EGTM) (Duffy, M. J., et al., Eur. J. Cancer 39 (2003) 718-727).

At present, primarily diagnostic blood tests based on the detection of carcinoembryonic antigen (CEA), a tumor-associated glycoprotein, are available to assist diagnosis in the field of CRC. CEA is increased in 95% of tissue samples obtained from patients with colorectal, gastric, and pancreatic cancers and in the majority of breast, lung, and head and neck carcinomas (Goldenberg, D. M., et al., J. Natl. Cancer Inst. (Bethesda) 57 (1976) 11-22). Elevated CEA levels have also been reported in patients with nonmalignant disease, and many patients with newly detected colorectal cancer have normal CEA levels in the serum, especially during the early stage of the disease (Carriquiry, L. A., and Pineyro, A., Dis. Colon Rectum 42 (1999) 921-929; Herrera, M. A., et al., Ann. Surg. 183 (1976) 5-9; Wanebo, H. J., et al., N. Engl. J. Med. 299 (1978) 448-451; Wanebo, H. J., et al., supra). The utility of CEA as measured from serum or plasma in detecting recurrences is reportedly controversial and has yet to be widely applied (Martell, R. E., et al., Int. J. Biol. Markers 13 (1998) 145-149; Moertel, C. G., et al., JAMA 270 (1993) 943-947).

In light of the available data, serum CEA determination possesses neither the sensitivity nor the specificity to enable its use as a screening test for colorectal cancer in the asymptomatic population (Reynoso, G., et al., JAMA 220 (1972) 361-365; Sturgeon, C., Clinical Chemistry 48 (2002) 1151-1159).

Whole blood, serum or plasma are the most widely used sources of sample in clinical routine. The identification of an early CRC tumor marker that would aid in the reliable cancer detection or provide early prognostic information could lead to a diagnostic assay that would greatly aid in the diagnosis and in the management of this disease. Therefore, an urgent clinical need exists to improve the in vitro assessment of CRC. It is especially important to improve the early diagnosis of CRC, since for patients diagnosed early on chances of survival are much higher as compared to those diagnosed at a progressed stage of disease.

It was the task of the present invention to investigate whether a biochemical marker can be identified which may be used in assessing CRC.

SUMMARY OF THE INVENTION

Surprisingly, it has been found that use of the marker CYFRA 21-1 can at least partially overcome the problems known from the state of the art.

The present invention relates to a method for assessing colorectal cancer in vitro comprising a) measuring in a sample the concentration of CYFRA 21-1, and b) using the concentration determined in step (a) in the assessment of colorectal cancer.

The present invention is also directed to a method for assessing CRC in vitro by biochemical markers, comprising measuring in a sample the concentration of CYFRA 21-1 and of one or more other marker of CRC and using the concentrations determined in the assessment of CRC.

The present invention also relates to the use of a marker panel comprising at least CYFRA 21-1 and NSE in the assessment of CRC.

The present invention also relates to the use of a marker panel comprising at least CYFRA 21-1 and ASC in the assessment of CRC.

The present invention also relates to the use of a marker panel comprising at least CYFRA 21-1 and OPN in the assessment of CRC.

The present invention also relates to the use of a marker panel comprising at least CYFRA 21-1 and FERR in the assessment of CRC.

The present invention also provides a kit for performing the method according to the present invention comprising at least the reagents required to specifically measure CYFRA 21-1 and NSE, respectively, and optionally auxiliary reagents for performing the measurement.

The present invention also provides a kit for performing the method according to the present invention comprising at least the reagents required to specifically measure CYFRA 21-1 and ASC, respectively, and optionally auxiliary reagents for performing the measurement.

The present invention also provides a kit for performing the method according to the present invention comprising at least the reagents required to specifically measure CYFRA 21-1 and OPN, respectively, and optionally auxiliary reagents for performing the measurement.

The present invention also provides a kit for performing the method according to the present invention comprising at least the reagents required to specifically measure CYFRA 21-1 and FERR, respectively, and optionally auxiliary reagents for performing the measurement.

In a further preferred embodiment the present invention relates to a method for assessing colorectal cancer in vitro comprising the steps of (a) measuring in a sample the concentration of CYFRA 21-1, (b) optionally measuring in the sample the concentration of one or more other marker of colorectal cancer, and (c) using the concentrations determined in step (a) and optionally step (b) in the assessment of colorectal cancer.

DETAILED DESCRIPTION OF THE INVENTION

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker.

The term "marker" or "biochemical marker" as used herein refers to a molecules to be used as a target for analyzing patient test samples. Examples of such molecular targets are proteins or polypeptides themselves as well as antibodies present in a sample. Proteins or polypeptides used as a marker in the present invention are contemplated to include any variants of said protein as well as fragments of said protein or said variant, in particular, immunologically detectable fragments. One of skill in the art would recognize that proteins which are released by cells or present in the extracellular matrix which become damaged, e.g., during inflammation could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but differ in their PI or MW, or both (e.g., as a result of alternative mRNA or pre-mRNA processing, e.g. alternative splicing or limited proteolysis) and in addition, or in the alternative, may arise from differential post-translational modification (e.g., glycosylation, acylation, and/or phosphorylation).

The term "assessing colorectal cancer" is used to indicate that the method according to the present invention will, alone or together with other markers or variables, e.g., the criteria set forth by the UICC (see above), e.g., aid the physician to establish or confirm the absence or presence of CRC or aid the physician in the prognosis, the monitoring of therapy efficacy (e.g. after surgery, chemotherapy or radiotherapy) and the detection of recurrence (follow-up of patients after therapy).

The term "sample" as used herein refers to a biological sample obtained for the purpose of evaluation in vitro. In the methods of the present invention, the sample or patient sample preferably may comprise any body fluid. Preferred test samples include blood, serum, plasma, urine, saliva, and synovial fluid. Preferred samples are whole blood, serum, plasma or synovial fluid, with plasma or serum being most preferred.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

In a preferred embodiment the present invention relates to a method for assessing CRC in vitro by biochemical markers, comprising measuring in a sample the concentration of CYFRA 21-1 and using the concentration determined in the assessment of CRC.

An assay for CYFRA 21-1 specifically measures a soluble fragment of cytokeratin 19 as present in the circulation. The measurement of CYFRA 21-1 is typically based upon two monoclonal antibodies (Bodenmueller, H., et al., Int. J. Biol. Markers 9 (1994) 75-81). In the CYFRA 21-1 assay from Roche Diagnostics, Germany, the two specific monoclonal antibodies (KS 19.1 and BM 19.21) are used and a soluble fragment of cytokeratin 19 having a molecular weight of approx. 30,000 daltons is measured.

Cytokeratins are structural proteins forming the subunits of epithelial intermediary filaments. Twenty different cytokeratin polypeptides have so far been identified. Due to their specific distribution patterns they are eminently suitable for use as differentiation markers in tumor pathology. Intact cytokeratin polypeptides are poorly soluble, but soluble fragments can be detected in serum (Bodenmueller, H., et al., supra).

CYFRA 21-1 is a well-established marker for Non-Small-Cell Lung Carcinoma (NSCLC). The main indication for CYFRA 21-1 is monitoring the course of non-small cell lung cancer (NSCLC) (Sturgeon, C., Clinical Chemistry 48 (2002) 1151-1159).

In primary diagnosis high CYFRA 21-1 serum levels indicate an advanced tumor stage and a poor prognosis in patients with non-small-cell lung cancer (van der Gaast, A., et al., Br. J. Cancer 69 (1994) 525-528). A normal or only slightly elevated value does not rule out the presence of a tumor.

Successful therapy is documented by a rapid fall in the CYFRA 21-1 serum level into the normal range. A constant CYFRA 21-1 value or a slight or only slow decrease in the CYFRA 21-1 value indicates incomplete removal of a tumor or the presence of multiple tumors with corresponding therapeutic and prognostic consequences. Progression of the disease is often shown earlier by increasing CYFRA 21-1 values than by clinical symptomatology and imaging procedures.

It is accepted that the primary diagnosis of pulmonary carcinoma should be made on the basis of clinical symptomatology, imaging or endoscopic procedures and intraoperative findings. An unclear circular focus in the lung together with CYFRA 21-1 values>30 ng/mL indicates with high probability the existence of primary bronchial carcinoma.

CYFRA 21-1 is also suitable for course-monitoring in myoinvasive cancer of the bladder. Good specificity is shown by CYFRA 21-1 relative to benign lung diseases (pneumonia, sarcoidosis, tuberculosis, chronic bronchitis, bronchial asthma, emphysema).

Slightly elevated values (up to 10 ng/mL) are rarely found in marked benign liver diseases and renal failure. There is no correlation with sex, age or smoking. The values for CYFRA 21-1 are also unaffected by pregnancy.

Recently it has been found that CYFRA also is of use in detecting disease relapse and assessing treatment efficacy in the field of breast cancer (Nakata, B., et al., British J. of Cancer (2004) 1-6).

CYFRA 21-1 has been measured on an Elecsys® analyzer using Roche product number 11820966 according to the manufacturers instructions.

As mentioned further above CYFRA 21-1 is an established marker in the field of NSCLC. When developing and establishing CYFRA 21-1 for NSCLC, non-malignant disease controls derived from patients with certain lung non-malignant diseases have been used. This has been considered important to differentiate benign from malign lung diseases (H. Bodenmüller, et al., supra).

The inventors of the present invention have surprisingly been able to detect the marker CYFRA 21-1 in a significant percentage of samples derived from patients with CRC. Even more surprising they have been able to demonstrate that the presence of CYFRA 21-1 in such liquid sample obtained from an individual can be used in the assessment of colorectal cancer.

It also has been found that the cut-off value for CYFRA 21-1 in the field of colorectal cancer should be considerably lower as established for NSCLC. Both healthy controls, as well as controls obtained from patients with non-malignant colon diseases have been used in this investigation and confirmed these findings. The finding that a lower cut-off applies for CYFRA 21-1 in the field of CRC is most likely also at least part of the explanation for the surprising finding that CYFRA 21-1 alone, but also in combination with other markers should be considered a marker of great potential in the field of CRC. As shown in the examples section CYFRA 21-1 alone is of significant utility in CRC because at a specificity of about 90% the sensitivity is almost 60%.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for CRC. As the skilled artisan will appreciate, no biochemical marker, for example in the field of CRC, is diagnostic with 100% specificity and at the same time 100% sensitivity for a given disease. Rather biochemical markers e.g. are used to assess with a certain likelihood or predictive value the presence or absence of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then interpreted independently using an individual cut-off for each marker or they are combined for interpretation.

In a further preferred embodiment the assessment of CRC according to the present invention is performed in a method comprising measuring in a sample the concentration of a) CYFRA 21-1, b) optionally one or more other marker of colorectal cancer, and c) using the concentration determined in step (a) and optionally step (b) in the assessment of colorectal cancer.

Preferably the method for assessment of CRC is performed by measuring the concentration of CYFRA 21-1 and of one or more other marker and by using the concentration of CYFRA 21-1 and of the one or more other marker in the assessment of CRC.

The present invention is also directed to a method for assessing CRC in vitro by biochemical markers, comprising measuring in a sample the concentration of CYFRA 21-1 and of one or more other marker of CRC and using the concentrations determined in the assessment of CRC.

According to the data shown in the Example section the marker CYFRA 21-1, both in the univariate analysis as well as in the multivariate analysis performed, has (at a specificity of about 90%) a remarkable sensitivity for CRC of almost 60% and in this respect was found superior as compared to other markers investigated. In the assessment of CRC the marker CYFRA 21-1 will be of advantage in one or more of the following aspects: screening; diagnostic aid; prognosis; monitoring of therapy, and follow-up.

Screening

CRC is the second most common malignancy of both males and females in developed countries. Because of its high prevalance, its long asymptomatic phase and the presence of premalignant lesions, CRC meets many of the criteria for screening. Clearly, a serum tumour marker which has acceptable sensitivity and specificity would be more suitable for screening than either FOB testing or endoscopy.

As the data given in the Examples section demonstrate CYFRA 21-1 alone will not suffice to allow for a general screening e.g. of the at risk population for CRC. Most likely no single biochemical marker in the circulation will ever meet the sensitivity and specificity criteria required for screening purposes. Rather it has to be expected that a marker panel will have to be used in CRC screening. The data established in the present invention indicate that the marker CYFRA 21-1 will form an integral part of a marker panel appropriate for screening purposes. The present invention therefore relates to the use of CYFRA 21-1 as one marker of a CRC marker panel for CRC screening purposes. The present data further indicate that certain combinations of markers will be advantageous in the screening for CRC. Therefore the present invention also relates to the use of a marker panel comprising CYFRA 21-1 and NSE, or of a marker panel comprising CYFRA 21-1 and ASC, or of a marker panel comprising CYFRA 21-1 and NSE and ASC for the purpose of screening for CRC.

Diagnostic Aid

Preoperative CEA values are of limited diagnostic value. Nonetheless the European Committee on Tumor Markers (ECTM) recommends the CFA should be measured before surgery in order to establish a baseline value and for assessing the prognosis. Since CYFRA 21-1 as a single marker according to the data of the present invention might be at least as good a single marker as CEA or even superior it has to be expected that CYFRA 21-1 will be used as a diagnostic aid, especially by establishing a baseline value before surgery.

The present invention thus also relates to the use of CYFRA 21-1 for establishing a baseline value before surgery for CRC.

Prognosis

The gold standard for determining prognosis in patients with CRC is the extend of disease as defined by the Dukes', TNM or other staging systems. If a marker such as CEA is to be used for predicting outcome, it must: provide stronger prognostic information than that offered by existing staging systems, provide information independent of the existing systems or provide prognostic data within specific subgroups defined by existing criteria, e.g. in Dukes' B or node-negative patients.

Recently, an American Joint Committee on Cancer (AJCC) Concensus Conference suggested that CEA should be added to the TNM staging system for colorectal cancer. The CEA level should be designated as follows: CX, CEA cannot be assessed; CO, CEA not elevated (<5 µg/l) or CEA1, CEA elevated (>5 µg/l) (Compton, C., et al., Cancer 88 (2000) 1739-1757).

As CYFRA 21-1 alone significantly contributes to the differentiation of CRC patients from healthy controls or from healthy controls plus non-malignant colon diseases, it has to be expected that it will aid in assessing the prognosis of patients suffering from CRC. The level of preoperative CYFRA 21-1 will most likely be combined with one or more other marker for CRC and/or the TNM staging system, as recommended for CEA by the AJCC. In a preferred embodiment CYFRA 21-1 is used in the prognosis of patients with CRC.

Monitoring of Chemotherapy

A number of reports have described the use of CEA in monitoring the treatment of patients with advanced CRC (for review, see Refs. Duffy, M. J., Clin. Chem. 47 (2001) 625-630; Fletcher, R. H., Ann. Int. Med. 104 (1986) 66-73; Anonymous, J. Clin. Oncol. 14 (1996) 2843-2877). Most of these were retrospective, non-randomized and contained small numbers of patients. These studies suggested: a) that patients with a decrease in CEA levels while receiving chemotherapy generally had a better outcome than those patients whose CEA levels failed to decrease and (b) for almost all patients, increases in CEA levels were associated with disease progression.

Due to the data shown in the example section, it has to be expected that CYFRA 21-1 will be at least as good a marker for monitoring of chemotherapy as CEA. The present invention therefore also relates to the use of CYFRA 21-1 in the monitoring of CRC patients under chemotherapy.

Follow-up

Approximately 50% of patients who undergo surgical resection aimed at cure, later develop recurrent or metastatic disease (Berman, J. M., et al., Lancet 355 (2000) 395-399). Most of these relapses occur within the first 2-3 years of diagnosis and are usually confined to the liver, lungs or locoregional areas. Since recurrent/metastatic disease is invariably fatal, considerable research has focused on its identification at an early and thus potentially treatable stage. Consequently, many of these patients undergo a postoperative surveillance program which frequently includes regular monitoring with CEA.

Serial monitoring with CEA has been shown to detect recurrent/metastatic disease with a sensitivity of approximately of 80%, specificity of approximately 70% and provides an average lead-time of 5 months (for review, see Duffy, M. J., et al., supra, and Fletcher, R. H., supra). Furthermore, CEA was the most frequent indicator of recurrence in asymptomatic patients (Pietra, N., et al., Dis. Colon Rectum 41 (1998) 1127-1133 and Graham, R. A., et al., Ann. Surg. 228 (1998) 59-63) and was more cost-effective than radiology for the detection of potentially curable recurrent disease. As regards sites of recurrence/metastasis, CEA was most sensitive (almost 100%) for the detection of liver metastasis. On the other hand, CEA was less reliable for diagnosing locoregional recurrences, the sensitivity being only approximately 60% (Moertel, C. G., et al., Jama 270 (1993) 943-947).

As a compromise between patient convenience, costs and efficiency of disease detection, the EGTM Panel like the ASCO Panel (Anonymous, J. Clin. Oncol. 14 (1996) 2843-2877) suggests that CEA testing be carried out every 2-3 months for at least 3 years after the initial diagnosis. After 3 years, testing could be carried out less frequently, e.g. every 6 months. No evidence exists, however, to support this frequency of testing.

As the above discussion of the state of the art shows, that the follow-up of patients with CRC after surgery is one of the most important fields of use for an appropriate biochemical marker. Due to the high sensitivity of CYFRA 21-1 in the CRC patients investigated it is expected that CYFRA 21-1 alone or in combination with one or more other marker will be of great help in the follow-up of CRC patients, especially in CRC patients after surgery. The use of a marker panel comprising CYFRA 21-1 and one or more other marker of CRC in the follow-up of CRC patients represents a further preferred embodiment of the present invention.

The present invention discloses and therefore in a preferred embodiment relates to the use of CYFRA 21-1 in the diagnostic field of CRC or in the assessment of CRC, respectively.

In yet a further preferred embodiment the present invention relates to the use of CYFRA 21-1 as a marker molecule for colorectal cancer in combination with one or more marker molecules for colorectal cancer in the assessment of colorectal cancer from a liquid sample obtained from an individual. In this regard, the expression "one or more" denotes 1 to 20, preferably 1 to 10, preferably 1 to 5, more preferred 3 or 4. CYFRA 21-1 and the one or more other marker form a CRC marker panel.

Thus, a preferred embodiment of the present invention is the use of CYFRA 21-1 as a marker molecule for colorectal cancer in combination with one or more marker molecules for colorectal cancer in the assessment of colorectal cancer from a liquid sample obtained from an individual. Preferred selected other CRC markers with which the measurement of CYFRA 21-1 may be combined are NSE, ASC, NMMT, CA 19-9, CA 72-4, and/or CEA. Yet further preferred the marker panel used in the assessment of CRC comprises CYFRA 21-1 and at least one other marker molecule selected from the group consisting of NSE, ASC and NMMT.

The markers which preferably are combined with CYFRA 21-1 or which form part of the CRC marker panel comprising CYFRA 21-1, respectively, are discussed in more detail below.

OPN

OPN (osteopontin) is a glyco-phosphoprotein that is expressed and secreted by numerous human cancers. OPN is found in normal plasma, urine, milk and bile (U.S. Pat. No. 6,414,219; U.S. Pat. No. 5,695,761; Denhardt, D. T. & Guo, X., FASEB J. 7 (1993) 1475-1482; Oldberg, A., et al., PNAS 83 (1986) 8819-8823; Oldberg, A., et al., J. Biol. Chem. 263 (1988) 19433-19436; Giachelli, C. M., et al., Trends Cardiovasc. Med. 5 (1995) 88-95). The human OPN protein and cDNA have been isolated and sequenced (Kiefer M. C., et al., Nucl. Acids Res. 17 (1989) 3306.

OPN functions in cell adhesion, chemotaxis, macrophage-directed interleukin-10 (IL-10) suppression, stress-dependent angiogenesis, prevention of apoptosis, and anchorage-independent growth of tumor cells by regulating cell-matrix interactions and cellular signaling through binding with integrin and CD44 receptors. While constitutive expression of OPN exists in several cell types, induced expression has been detected in T-lymphocytes, epidermal cells, bone cells, macrophages, and tumor cells in remodeling processes such as inflammation, ischemia-reperfusion, bone resorption, and tumor progression (reviewed by Wai, P. Y. & Kuo P. C. J. Surg. Res. 121 (2004) 228-241).

OPN is known to interact with a number of integrin receptors. Increased OPN expression has been reported in a number of human cancers, and its cognate receptors (av-b3, av-b5, and av-b1 integrins and CD44) have been identified. In vitro studies by Irby, R. B., et al., Clinical & Experimental Metastasis 21 (2004) 515-523 indicate that both endogenous OPN expression (via stable transfection) as well as exogenous OPN (added to culture medium) enhanced the motility and invasive capacity of human colon cancer cells in vitro. OPN appeared to regulate motility though interaction with CD44. OPN expression also reduced intercellular (homotypic) adhesion, which is regarded as a characteristic of metastatic cancer cells. Stable transfection of four poorly tumorigenic human colon cancer cell lines with OPN also resulted in enhanced tumorigenicity in vivo with increased proliferation and increased CD31 positive microvessel counts, concordant with the degree of OPN expression.

Mor, G., et al., PNAS 102 (2005) 7677-7682 report a blood (serum) test for the early diagnosis of epithelial ovarian cancer based on the simultaneous quantitation of OPN and three other analytes.

NSE

NSE (neuron-specific enolase), also known as the glycolytic enzyme enolase (2-phospho-D-glycerate hydrolase, EC 4.2.1.11, molecular weight approx. 80 kD) occurs in a variety of dimeric isoforms comprising three immunologically different subunits termed $\alpha$, $\beta$, and $\gamma$. The $\alpha$-subunit of enolase occurs in numerous types of tissue in mammals, whereas the $\beta$-subunits found mainly in the heart and in striated musculature. The enolase isoforms $\alpha\gamma$ and $\gamma\gamma$, which are referred to as neuron-specific enolase (NSE) or $\gamma$-enolase, are primarily detectable in high concentrations in neurons and neuro-endocrine cells as well as in tumors originating from them (Lamerz R., NSE (Neuronen-spezifische Enolase), $\gamma$-Enolase, In: Thomas L. (ed.), Clinical Laboratory Diagnosis, TH-Books, Frankfurt, $1^{st}$ English Edition 1998: 979-981, 5. deutsche Auflage 1998: 1000-1003).

NSE is described as the marker of first choice in the monitoring of small cell bronchial carcinoma (Lamerz R., supra), whereas CYFRA 21-1 is superior to NSE for non-small cell bronchial carcinoma (Ebert, W., et al., Eur. J. Clin. Chem. Clin. Biochem 32 (1994) 189-199).

Elevated NSE concentrations are found in 60-81% of cases of small cell bronchial carcinoma.

For NSE there is no correlation to the site of metastasis or to cerebral metastasis, but there is good correlation to the clinical stage, i.e. the extent of the disease.

In response to chemotherapy there is a temporary rise in the NSE level 24-72 hours after the first therapy cycle as a result of cytolysis of the tumor cells. This is followed within a week or by the end of the first therapy cycle by a rapid fall in the serum values (which were elevated prior to therapy). By contrast, non-responders to therapy display levels which are constantly elevated or fail to fall into the reference range. During remission, 80-96% of the patients have normal values. Rising NSE values are found in cases of relapse. The rise occurs in some cases with a latent period of 1-4 months, is often exponential (with a doubling time of 10-94 days) and correlates with the survival period. NSE is useful as a single prognostic factor and activity marker during the monitoring of therapy and the course of the disease in small cell bronchial carcinoma: diagnostic sensitivity 93%, positive predictive value 92% (Lamerz R., supra).

In neuroblastoma NSE serum values above 30 ng/ml are found in 62% of the affected children. The medians rise in accordance with the stage of the disease. There is a significant correlation between the magnitude or frequency of pathological NSE values and the stage of disease; there is an inverse correlation with illness-free survival.

68-73% of the patients with seminoma have a clinically significant NSE elevation (Lamerz R., supra). There is a utilizable correlation with the clinical course of the disease.

NSE has also been measured in other tumors: Non-pulmonary malignant diseases show values above 25 ng/ml in 22% of the cases (carcinomas in all stages). Brain tumors such as glioma, miningioma, neurofibroma, and neurinoma are only occasionally accompanied by elevated serum NSE values. In primary brain tumors or brain metastasis and in malignant melanoma and phaeochromocytoma, elevated NSE-values can occur in the CSF (cerebrospinal fluid). Increased NSE concentrations have been reported for 14% of organ-restricted and 46% of metastasizing renal carcinomas, with a correlation to the grade as an independent prognosis factor.

In benign disease elevated serum NSE concentrations (>12 ng/ml) have been found in patients with benign pulmonary diseases and cerebral diseases. Elevated values, mainly in the liquor, have been found in cerebrovascular meningitis, disseminated encephalitis, spinocerebellar degeneration, cerebral ischemia, cerebral infarction, intracerebral hematoma, subarachnoid hemorrhage, head injuries, inflammatory brain diseases, organic epilepsy, schizophrenia, and Jakob-Creutzfeld disease (Lamerz R., supra).

NSE has been measured on an Elecsys® analyzer using Roche product number 12133113 according to the manufacturers instructions.

CA 19-9

The CA 19-9 (carbohydrate antigen 19-9) values measured are defined by the use of the monoclonal antibody 1116-NS-19-9. The 1116-NS-19-9-reactive determinant in serum is mainly expressed on a mucin-like protein that contains a high number of CA 19-9 epitopes (Magnani J. L., Arch. Biochem. Biophys. 426 (2004) 122-131).

3-7% of the population have the Lewis a-negative/b-negative blood group configuration and are unable to express the mucin with the reactive determinant CA 19-9. This must be taken into account when interpreting the findings.

CA 19-9 containing mucins are expressed in fetal gastric, intestinal and pancreatic epithelia. Low concentrations can also be found in adult tissue in the liver, lungs, and pancreas (Stieber, P. and Fateh-Moghadam, A., Boeringer Mannheim, Cat. No. 1536869 (engl), 1320947 (dtsch). ISBN 3-926725-07-9 dtsch/engl., Juergen Hartmann Verlag, Marloffstein-Rathsberg (1993); Herlyn, M., et al., J. Clin. Immunol. 2 (1982) 135-140).

CA 19-9 assay values can assist in the differential diagnosis and monitoring of patients with pancreatic carcinoma (sensitivity 70-87%) (Ritts, R. E., Jr., et al., Int. J. Cancer 33 (1984) 339-345). There is no correlation between tumor mass and the CA 19-9 assay values. However, patients with CA 19-9 serum levels above 10,000 U/mL almost always have distal metastasis.

The determination of CA 19-9 cannot be used for the early detection of pancreatic carcinoma (Steinberg, W. M., et al., Gastroenterology 90 (1986) 343-349).

In hepatobiliary carcinoma the CA 19-9 values provide a sensitivity of 50-75%. The concomitant determination of CA 72-4 and CEA is recommended in case of gastric carcinoma. In colorectal carcinoma, determination of CEA alone is adequate; only in a limited number of the CEA-negative cases the determination of CA 19-9 can be useful.

As the mucin is excreted exclusively via the liver, even slight cholestasis can lead to clearly elevated CA 19-9 serum levels in some cases. Elevated CA 19-9 values are also found with a number of benign and inflammatory diseases of the gastrointestinal tract and the liver, as well as in cystic fibrosis.

CA 19-9 has been measured on a Elecsys® analyzer using Roche product number 11776193 according to the manufacturers instructions.

CEA

CEA (carcinoembryonic antigen) is a monomeric glycoprotein (molecular weight approx. 180,000 dalton) with a variable carbohydrate component of approx. 45-60% (Gold, P. and Freedman, S. O., J. Exp Med 121 (1965) 439-462).

CEA, like AFP, belongs to the group of carcinofetal antigens that are produced during the embryonic and fetal period. The CEA gene family consists of about 17 active genes in two subgroups. The first group contains CEA and the non-specific cross-reacting antigens (NCA); the second group contains the pregnancy-specific glycoproteins (PSG).

CEA is mainly found in the fetal gastrointestinal tract and in fetal serum. It also occurs in slight quantities in intestinal, pancreatic, and hepatic tissue of healthy adults. The formation of CEA is repressed after birth, and accordingly serum CEA values are hardly measurable in healthy adults.

High CEA concentrations are frequently found in cases of colorectal adenocarcinoma (Stieber, P. and Fateh-Moghadam, A., supra). Slight to moderate CEA elevations (rarely>10 ng/mL) occur in 20-50% of benign diseases of the intestine, the pancreas, the liver, and the lungs (e.g. liver cirrhosis, chronic hepatitis, pancreatitis, ulcerative colitis, Crohn's Disease, emphysema (Stieber, P., and Fateh-Moghadam, A., supra). Smokers also have elevated CEA values.

The main indication for CEA determinations is therapy management and the follow-up of patients with colorectal carcinoma.

CEA determinations are not recommended for cancer-screening in the general population. CEA concentrations within the normal range do not exclude the possible presence of a malignant disease.

The antibodies in assay manufactured by Roche Diagnostics react with CEA and (as with almost all CEA detection methods) with the merconium antigen (NCA2). Cross-reactivity with NCA1 is 0.7% (Hammarstrom, S., et al., Cancer Res. 49 (1989) 4852-4858; and Bormer, O. P., Tumor Biol. 12 (1991) 9-15).

CEA has been measured on an Elecsys® analyzer using Roche product number 11731629 according to the manufacturers instructions.

ASC

The "apoptosis-associated speck-like protein containing a caspase-associated recruitment domain" (ASC), is also known as "target of methylation-induced silencing 1" (TMS1) (Swiss-PROT: Q9ULZ3). ASC has a theoretical molecular weight of 21,627 Da and a theoretical isoelectric point of pH 6.29.

Caspase-associated recruitment domains (CARDs) mediate the interaction between adaptor proteins such as APAF1 (apoptotic protease activating factor 1) and the pro-form of caspases (e.g., CASP 9) participating in apoptosis. ASC is a member of the CARD-containing adaptor protein family.

By immunoscreening a promyelocytic cell line, Masumoto et al. isolated a cDNA encoding ASC. The deduced 195-amino acid protein contains an N-terminal pyrin-like domain (PYD) and an 87-residue C-terminal CARD. Western blot analysis showed expression of a 22-kDa protein and indicated that ASC may have proapoptotic activity by increasing the susceptibility of leukemia cell lines to apoptotic stimuli by anticancer drugs (Masumoto, J., et al., J. Biol. Chem. 274 (1999) 33835-33838).

Methylation-sensitive restriction PCR and methylation-specific PCR (MSP) analyses by Conway et al. indicated that silencing of ASC correlates with hypermethylation of the CpG island surrounding exon1 and that overexpression of DNMT1 (DNA cytosine-5-methyltransferase-1) promotes hypermethylation and silencing of ASC. Breast cancer cell lines, but not normal breast tissue, exhibited complete methylation of ASC and expressed no ASC message. Expression of ASC in breast cancer cell lines inhibited growth and reduced the number of surviving colonies. Conway et al. concluded that ASC functions in the promotion of caspase-dependent apoptosis and that overexpression of ASC inhibits the growth of breast cancer cells (Conway, K. E., et al., Cancer Research 60 (2000) 6236-6242).

McConnell and Vertino showed that inducible expression of ASC inhibits cellular proliferation and induces DNA fragmentation that can be blocked by caspase inhibitor. Immunofluorescence microscopy demonstrated that induction of apoptosis causes a CARD-dependent shift from diffuse cytoplasmic expression to spherical perinuclear aggregates (McConnell, B. B., and Vertino, P. M., Cancer Research 60 (2000) 6243-6247). Moriani et al. observed methylation of ASC gene not only in breast cancer cells but also in gastric cancer. They suggested a direct role for aberrant methylation of the ASC gene in the progression of breast and gastric cancer involving down-regulation of the proapoptotic ASC gene (Moriani, R., et al., Anticancer Research 22 (2002) 4163-4168).

Conway et al. examined primary breast tissues for TMS1 methylation and compared the results to methylation in healthy tissues (Conway K. E., et al., Cancer Research 60 (2000) 6236-6242). Levine et al. found that ASC silencing was not correlated with methylation of specific CpG sites, but rather was associated with dense methylation of ASC CpG island. Breast tumor cell lines containing exclusively methylated ASC copies do not express ASC, while in partially methylated cell lines the levels of ASC expression are directly related to the percentage of methylated ASC allels present in the cell population (Levine, J. J., et al., Oncogene 22 (2003) 3475-3488).

Virmani et al. examined the methylation status of ASC in lung cancer and breast cancer tissue. They found that aberrant methylation of ASC was present in 46% of breast cancer cell lines and in 32% of breast tumor tissue. Methylation was rare in non-malignant breast tissue (7% (Virmani, A., et al., Int. J. Cancer 106 (2003) 198-204).

Shiohara et al. found out that up-regulation of ASC is closely associated with inflammation and apoptosis in human neutrophils (Shiohara, M., et al., Blood 98 (2001) 229a).

Masumoto et al. observed that high levels of ASC are abundantly expressed in epithelial cells and leucocytes (Masumoto, J., et al., Journal Histochem. Cytochem. 49 (2001) 1269-1275).

An in-house sandwich immunoassay has been developed for measurement of ASC. This assay is performed in a microtiter plate format. Streptavidin-coated microtiter plates are used. A biotinylated polyclonal antibody to ASC is used as a capturing antibody and a digoxigenylated polyclonal antibody to ASC is used as the second specific binding partner in this sandwich assay. The sandwich complex formed is finally visualized by an anti-digoxigenin horseradish peroxidase conjugate and an appropriate peroxidase substrate.

MASP

The protein MASP (maspin precursor; Swiss-PROT: P36952) is a 42-kDa protein that shares homology with the serpin superfamily of protease inhibitors. Immunostaining studies demonstrate that maspin is found in the extracellular matrix and at the plasma membrane (Zou, Z., et al., Science 263 (1994) 526-529).

The human MASP gene (SERPINB5 of PI5) was originally isolated from normal mammary epithelium by subtractive hybridization on the basis of its expression at the mRNA level (Zou et al., supra). Maspin was expressed in normal mammary epithelial cells but not in most mammary carcinoma cell lines. Zou et al. (supra) showed that its expression reduces the ability of transformed cells to induce tumor formation and metastasis, suggesting that the maspin gene encodes a tumor suppressor.

Bass, R., et al. (J. Biol. Chem. 277 (2002) 46845-46848) characterized eukaryotic maspin and found that it had no protease inhibitory effect against any of the proteolytic systems tested. It did, however, inhibit the migration of both tumor and vascular smooth muscle cells.

Song, S. Y., et al. (Digestive Diseases and Sciences 47 (2002) 1831-1835) studied the expression of maspin in colon cancers by immunohistochemical staining of tissue sections from adenomas, adenocarcinomas and metastatic adenocarcinomas. The immunoreactivity of maspin found by Song et al. (supra) was cytoplasmic, with some nuclear staining. More than 90% of adenoma, 75% of adenocarcinoma and 47% of metastatic carcinoma tissue sections stained positive for maspin. This study had the limitation that no quantitative assay system, such as western blot analysis, was used. The level of expression in comparison to the adjacent normal colon tissue was not assessed.

FERR

Ferritin (FERR) is a protein containing about 20% iron and is found in the intestines, the liver and the spleen. It is one of the chief forms in which iron is stored in the body. Body iron stores have been reported to increase the risk of colorectal neoplasms. In a study by Scholefield, J. H., et al. (Dis. Colon Rectum 41 (1998) 1029-1032) using samples from 148 patients (50 patients with proven colorectal cancer, 49 patients without colon disease, and patients with adenomas of the colon) serum ferritin was assayed. There were no significant differences in serum ferritin levels among any of the three groups.

NNMT

The protein nicotinamide N-methyltransferase (NNMT; Swiss-PROT; P40261) has an apparent molecular weight of 29.6 kDa and an isoelectric point of 5.56.

NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa, (Aksoy, S., et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A., et al., Jpn. J. Cancer Res. 89 (1998) 649-656). In a recent report, down-regulation of the NNMT gene in response to radiation in radiation sensitive cell lines was demonstrated (Kassem, H., et al., Int. J. Cancer 101 (2002) 454-460).

It has recently been found (WO 2004/057336) that NNMT will be of interest in the assessment of CRC. The immunoassay described in WO 2004/057336 has been used to measure the samples (CRC, healthy controls and non-malignant colon diseases) of the present study.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may e.g. the case when diagnosing an infectious disease, like AIDS.

Frequently, however, the combination of markers is evaluated. Preferably the values measured for markers of a marker panel, e.g. for CYFRA 21-1 and NSE, or for CYFRA 21-1 and OPN are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention e.g. to the absence or presence of CRC is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al., J. of Computational and Graphical Statistics, 12 (2003) 475-511; Friedman, J. H., J. of the American Statistical Association 84 (1989) 165-175; Hastie, T., Tibshirani, R., Friedman, J., The Elements of Statistical Learning, Springer Series in Statistics, 2001; Breiman, L., Friedman, J. H., Olshen, R. A., Stone, C. J. (1984) Classification and regression trees, California: Wadsworth; Breiman, L., Random Forests, Machine Learning 45 (2001) 5-32; Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

It is a preferred embodiment of the invention to use an optimized multivariate cut-off for the underlying combination of biological markers and to discriminate state A from state B, e.g. diseased from healthy. In this type of analysis the markers are no longer independent but form a marker panel. It could be established that combining the measurements of CYFRA 21-1 and NSE or ASC, respectively, does significantly improve the diagnostic accuracy for CRC as compared to either healthy controls or, as also assessed, as compared to healthy controls plus non-malignant disease controls. Alternatively, combining CYFRA 21-1 with OPN or with OPN and FERR improves diagnostic accuracy in a likewise setting. Especially the later finding is of great importance, because a patient with a non-malignant disease may require quite a different treatment as a patient with CRC.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1−specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1−specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1−specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One convenient goal to quantify the diagnostic accuracy of a laboratory test is to express its performance by a single number. Such an overall parameter e.g. is the so-called "total error" or alternatively the "area under the curve=AUC". The most common global measure is the area under the ROC plot. By convention, this area is always $\geq 0.5$ (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of CYFRA 21-1 with other recently discovered markers, like OPN, ASC or NNMT or with known markers like CEA and NSE, or with other markers of CRC yet to be discovered, leads and will lead, respectively, to further improvements in assessment of CRC.

The combination of the two markers CYFRA 21-1 and NSE significantly improves the diagnostic accuracy for CRC.

The combination of the two markers CYFRA 21-1 and ASC also significantly improves the diagnostic accuracy for CRC. In addition, the combination of the two markers CYFRA 21-1 and OPN significantly improves the diagnostic accuracy for CRC.

In a preferred embodiment the present invention relates to a method for improving the diagnostic accuracy for CRC versus healthy controls and/or patients suffering from non-malignant colon disease by measuring in a sample the concentration of at least CYFRA 21-1 and NSE, OPN or ASC, respectively and correlating the concentrations determined to the presence or absence of CRC, the improvement resulting in more patients being correctly classified as suffering from CRC versus healthy controls and/or patients suffering from non-malignant colon disease as compared to a classification based on any single marker investigated alone.

In a preferred method according to the present invention at least the concentration of the biomarkers CYFRA 21-1 and NSE, respectively, is determined and the marker combination is used in the assessment of CRC.

In a further preferred method according to the present invention at least the concentration of the biomarkers CYFRA 21-1 and ASC, respectively, is determined and the marker combination is used in the assessment of CRC.

In a further preferred method according to the present invention at least the concentration of the biomarkers CYFRA 21-1 and OPN, respectively, is determined and the marker combination is used in the assessment of CRC.

In yet a further preferred method according to the present invention at least the concentration of the biomarkers CYFRA 21-1, NSE and ASC, respectively, is determined and the marker combination is used in the assessment of CRC.

In yet a further preferred method according to the present invention at least the concentration of the biomarkers CYFRA 21-1, OPN and ASC, respectively, is determined and the marker combination is used in the assessment of CRC.

In yet a further preferred method according to the present invention at least the concentration of the biomarkers CYFRA 21-1, NSE and OPN, respectively, is determined and the marker combination is used in the assessment of CRC.

In yet a further preferred method according to the present invention at least the concentration of the biomarkers CYFRA 21-1, NNMT and OPN, respectively, is determined and the marker combination is used in the assessment of CRC.

In yet a further preferred method according to the present invention at least the concentration of the biomarkers CYFRA 21-1, MASP and OPN, respectively, is determined and the marker combination is used in the assessment of CRC.

In yet a further preferred method according to the present invention at least the concentration of the biomarkers CYFRA 21-1, FERR and OPN, respectively, is determined and the marker combination is used in the assessment of CRC.

The following examples, references, and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

1$^{st}$ Study Population

Samples derived from 109 well-characterized CRC patients with the UICC classification given in Table 1 have been used.

TABLE 1

1$^{st}$ study population:
CRC samples and corresponding UICC classification

| Stage according to UICC | Number of samples |
|---|---|
| UICC 0 | 3 |
| UICC I | 33 |
| UICC II | 23 |
| UICC III | 21 |
| UICC IV | 23 |
| without staging | 6 |
| total number of CRC samples | 109 |

The CRC samples of Table 1 have been evaluated in comparison to control samples obtained from healthy individual, patients with non-malignant colon diseases or in comparison to the pooled data obtained with the healthy and the non-malignant control samples. Table 2 gives an overview over the controls used.

TABLE 2

1$^{st}$ study population:
Healthy and non-malignant controls

| Type of control sample | Number of samples |
|---|---|
| healthy controls | 317 |
| divertikulosis | 50 |
| diverticulitis | 7 |
| colitis | 12 |
| CED | 10 |
| ulcer | 3 |
| others | 5 |
| all disease controls | 87 |

In the following examples data are presented using the data obtained from all the samples listed in Table 2 (i.e. data covering both healthy as well as non-malignant disease controls).

Example 2

Sensitivity for each marker has been calculated at a common specificity level of 90% for each individual marker tested. Table 3 gives the sensitivity over all UICC stages in percent for each of the most promising CRC markers.

TABLE 3

Sensitivity of single markers
in the 1$^{st}$ study population

| | Marker | | | | | |
|---|---|---|---|---|---|---|
| | NSE | ASC | NNMT | CA 19-9 | CEA | Cyfra |
| Sensitivity at 90% specificity | 18.9% | 54.1% | 55.0% | 32.1% | 46.8% | 57.8% |

As is readily obvious from Table 3, the marker CYFRA 21-1 (=CYFRA) has be found to have the highest sensitivity for CRC as compared to all the other markers investigated. The markers NNMT and ASC appear to have a comparable but slightly lower sensitivity and are followed by CEA.

Example 3

Marker Panels

The classification algorithms were generated with the Regularized Discriminant Analysis (RDA), which is a generalization of the common Discriminant Analysis, i.e. Quadratic- and Linear Discriminant Analysis (McLachlan, G. J., Discriminant Analysis and Statistical Pattern Recognition, Wiley Series in probability and mathematical statistics, 1992). In the RDA alternatives to the usual maximum likelihood (plug-in) estimates for the covariance matrices are used. These alternatives are characterized by two parameters $(\lambda, \gamma)$, the values of which are customized to individual situations by jointly minimizing a sample-based estimate of future misclassification risk (Friedman, J. H., Regularized Discriminant Analysis, J. of the American Statistical Association 84 (1989) 165-175). As an alternative method Support Vector Machines algorithms (Hastie, Trevor, Tibshirani, Robert, Friedman, Jerome, The Elements of Statistical Learning, Springer Series in Statistics, 2001) can be fitted with comparable classification results. The analysis by RDA has been based on 106 CRC samples, because for 3 out of the original 109 samples a marker value was missing.

The marker panels were stepwise constructed starting from the best single marker for the classification problem and ending when the increase in the sensitivity at a specificity level of about 90% does not change remarkably any more. In order to gain centralized distributions every single marker was transformed with the natural logarithmic function. 5-fold cross validation was used.

Table 4 presents the classification results of patients diagnosed with CRC versus controls including non-malignant colon diseases. The first marker selected by RDA was CYFRA 21-1, the second one NSE.

TABLE 4

Classification results on the training set of patients with CRC versus healthy controls and disease controls

| No of Markers | Marker or marker panel | Method (RDA) | Cut-off | TOTAL ERROR | Cross validation (5 fold) correct pos. Sensitivity | correct neg. Specificity |
|---|---|---|---|---|---|---|
| 1 | log CYFRA | $\lambda = 0.25, \gamma = 0$ | 2.8 | 0.16 | 59.7% | 90.3% |
| 2 | log CYFRA, log NSE | $\lambda = 0, \gamma = 0.75$ | 3.7 | 0.14 | 69.6% | 90.5% |
| 3 | log CYFRA, log NSE, log ASC | $\lambda = 0.5, \gamma = 0$ | 2.7 | 0.12 | 78.7% | 90.2% |
| 4 | log CYFRA, log NSE, log ASC, log NNMT | $\lambda = 0.5, \gamma = 0$ | 2.0 | 0.13 | 76.4% | 90% |

The marker panel CYFRA 21-1, NSE, and ASC in this analysis did yield the highest sensitivity at a specificity level of about 90%.

Various other marker markers have been evaluated in combination with CYFRA 21-1. As shown in Table 5, ASC in combination with CYFRA 21-1 also lead to a significant improvement in sensitivity, whereas the combination of CYFRA 21-1 with other candidate CRC markers appears to be less favorable.

TABLE 5

Classification results on the training set of patients diagnosed with CRC versus healthy controls and disease controls

| No of Markers | Marker or marker panel | Method (RDA) | Cut-off | TOTAL ERROR | Cross validation (5 fold) correct pos. Sensitivity | correct neg. Specificity |
|---|---|---|---|---|---|---|
| 2 | log CYFRA, log ASC | $\lambda = 0.75, \gamma = 1$ | 2.7 | 0.15 | 67.6% | 90.2% |
| 2 | log CYFRA, log NNMT | $\lambda = 1, \gamma = 0.25$ | 2.2 | 0.16 | 62.8% | 90.1% |
| 2 | log CYFRA, log CA19_9 | $\lambda = 0.75, \gamma = 1$ | 2.5 | 0.17 | 55.8% | 90.1% |
| 2 | log CYFRA, log CEA | $\lambda = 1, \gamma = 0.75$ | 2.5 | 0.17 | 54.6% | 90.5% |

Figure 1:
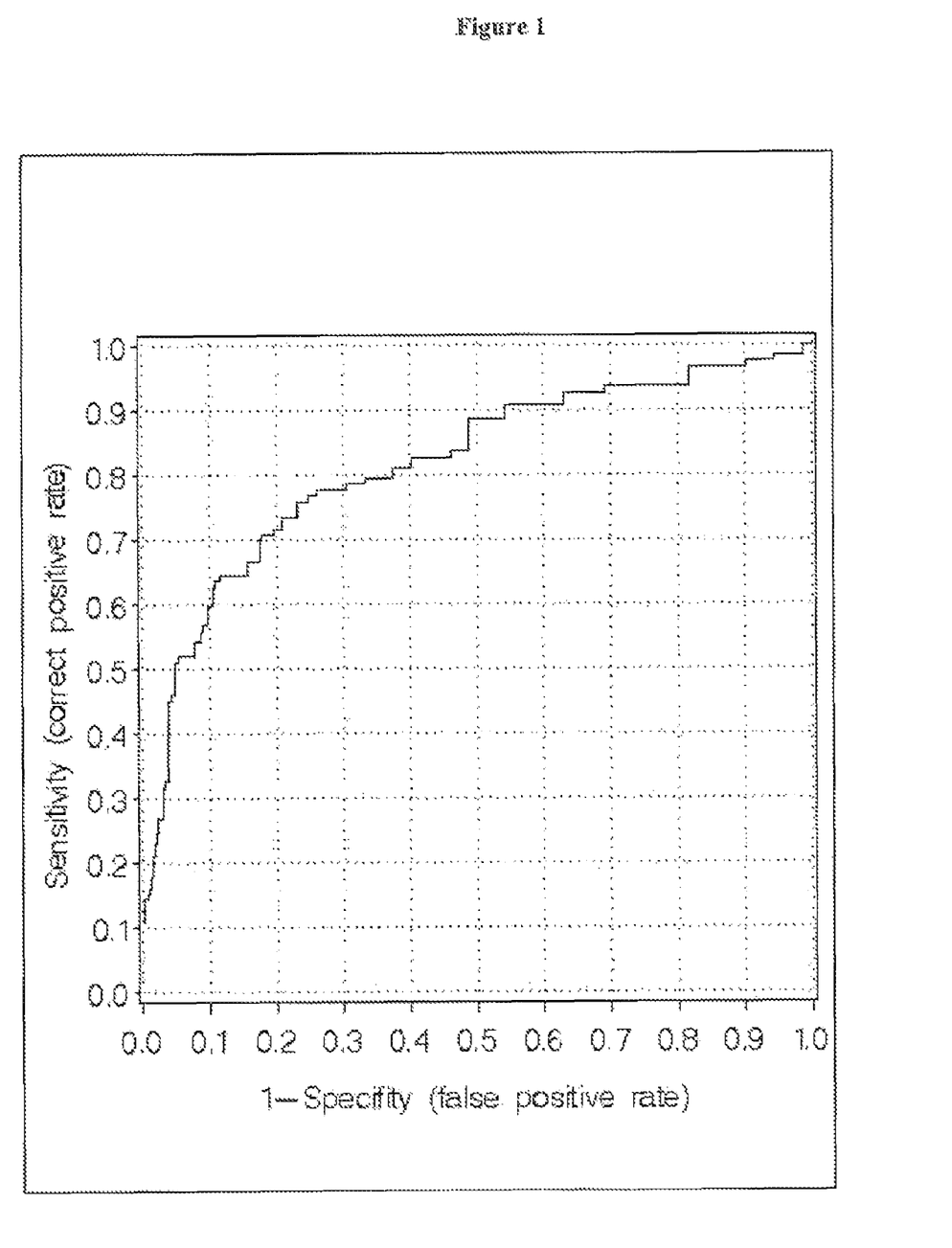
FIG. 1 ROC-analysis of patients diagnosed with CRC versus healthy controls and disease controls using log CYFRA 21-1 alone.
Figure 2:
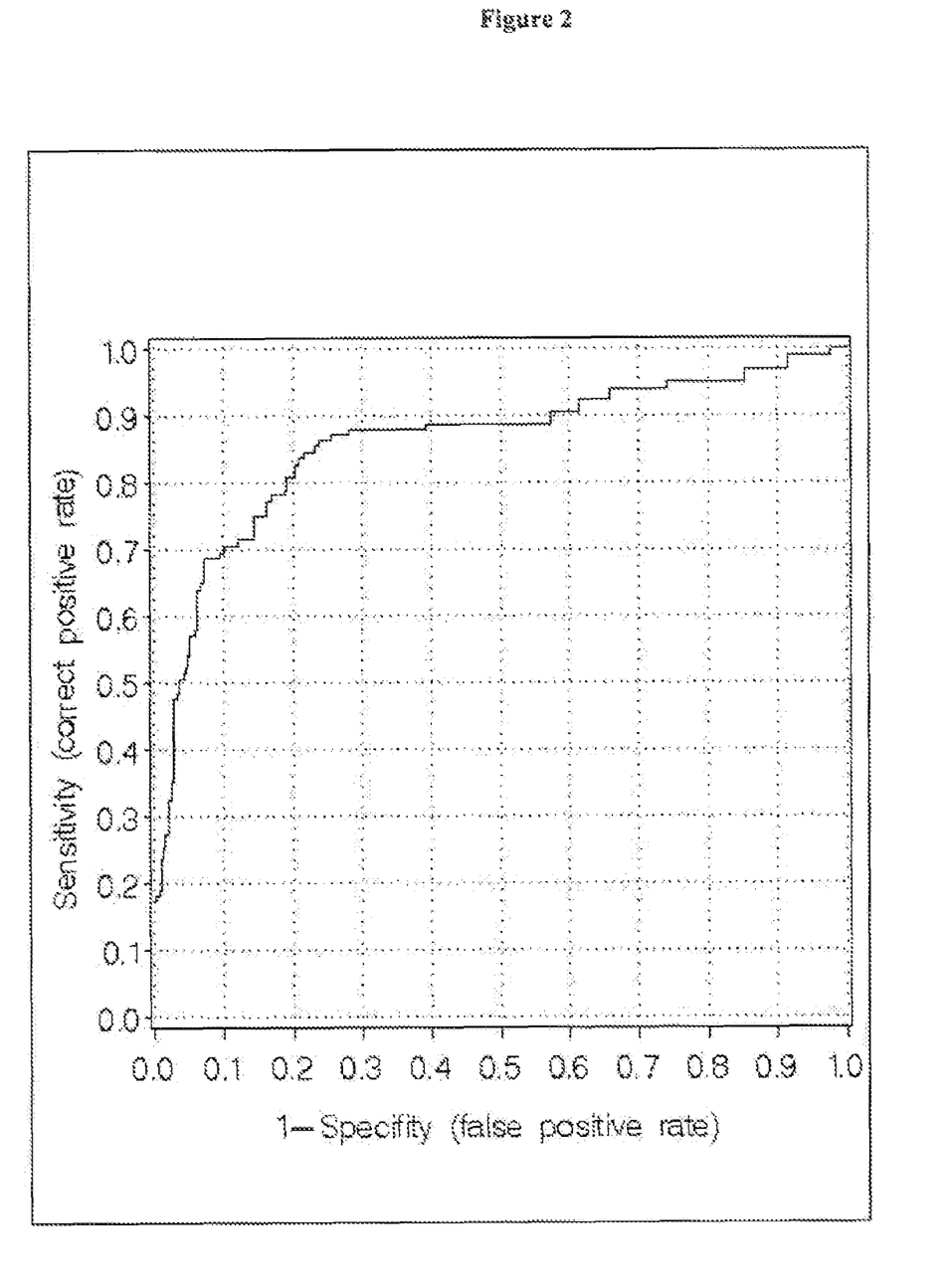
FIG. 2 ROC-analysis of patients diagnosed with CRC versus healthy controls and disease controls using the combination of log CYFRA 21-1 and log NSE.
Figure 3:
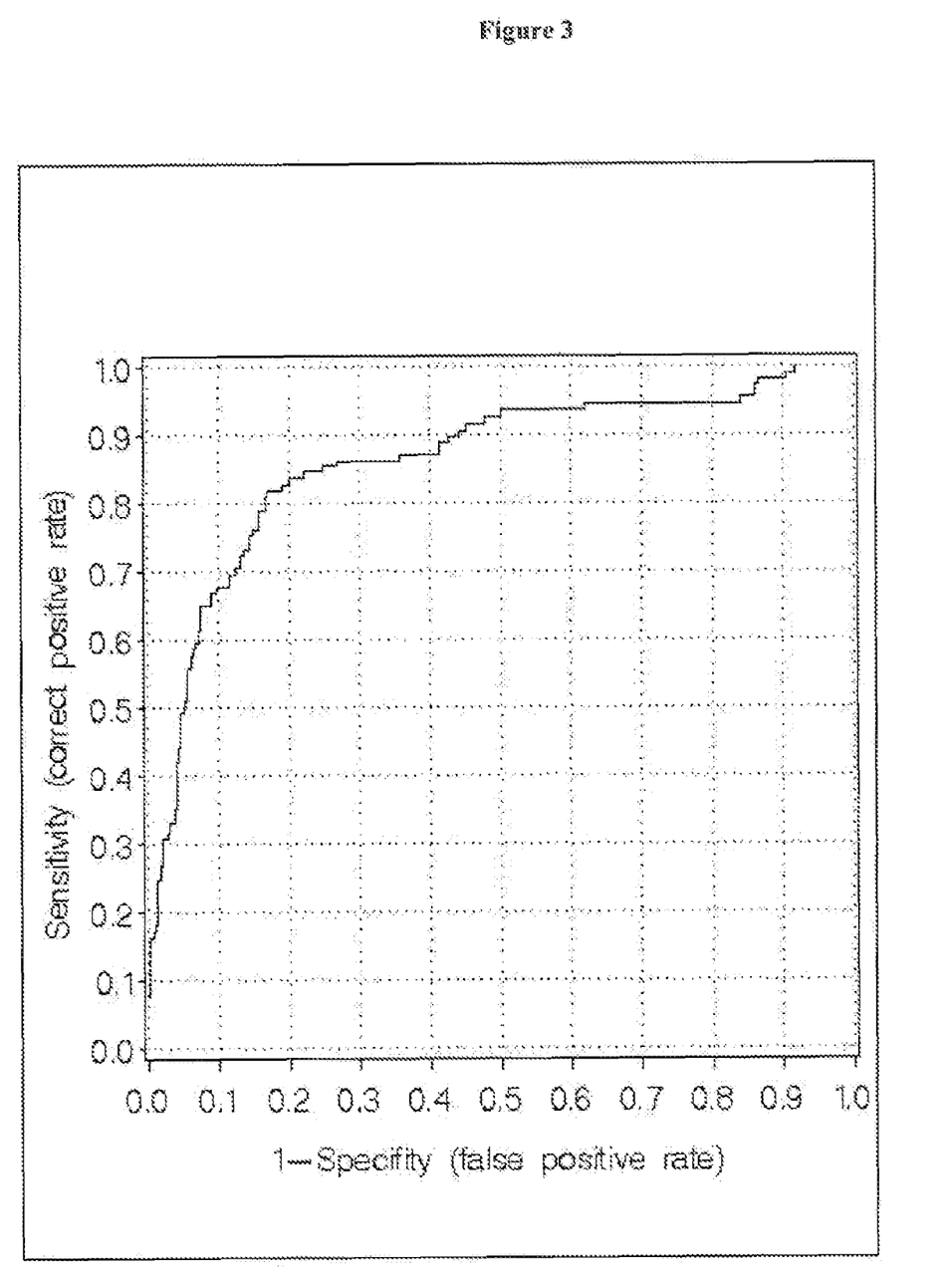
FIG. 3 ROC-analysis of patients diagnosed with CRC versus healthy controls and disease controls using the combination of log CYFRA 21-1 and log ASC.
Figure 4:
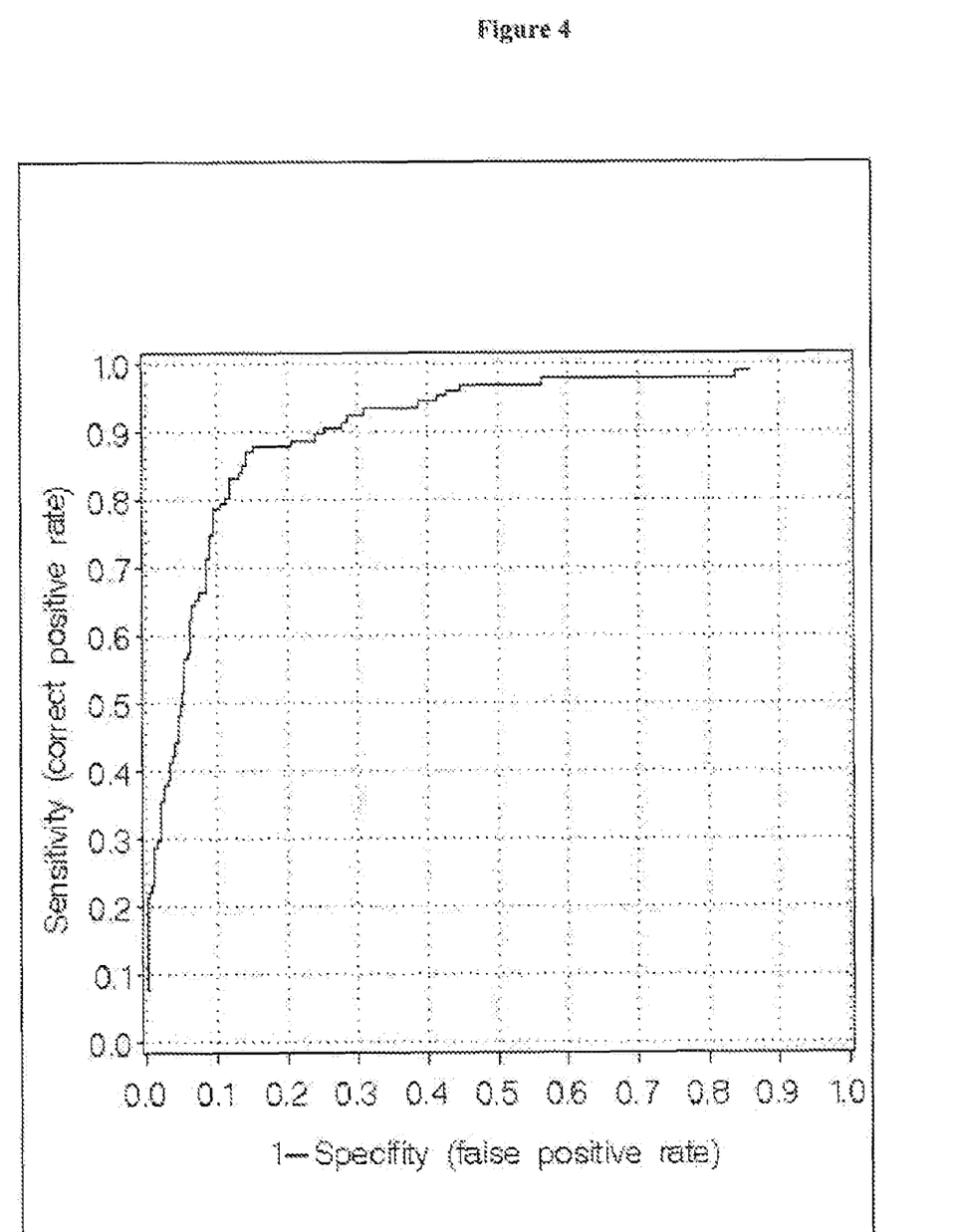
FIG. 4 ROC-analysis of patients diagnosed with CRC versus healthy controls and disease controls using the combination of log CYFRA 21-1, log NSE and log ASC.
Figure 5:
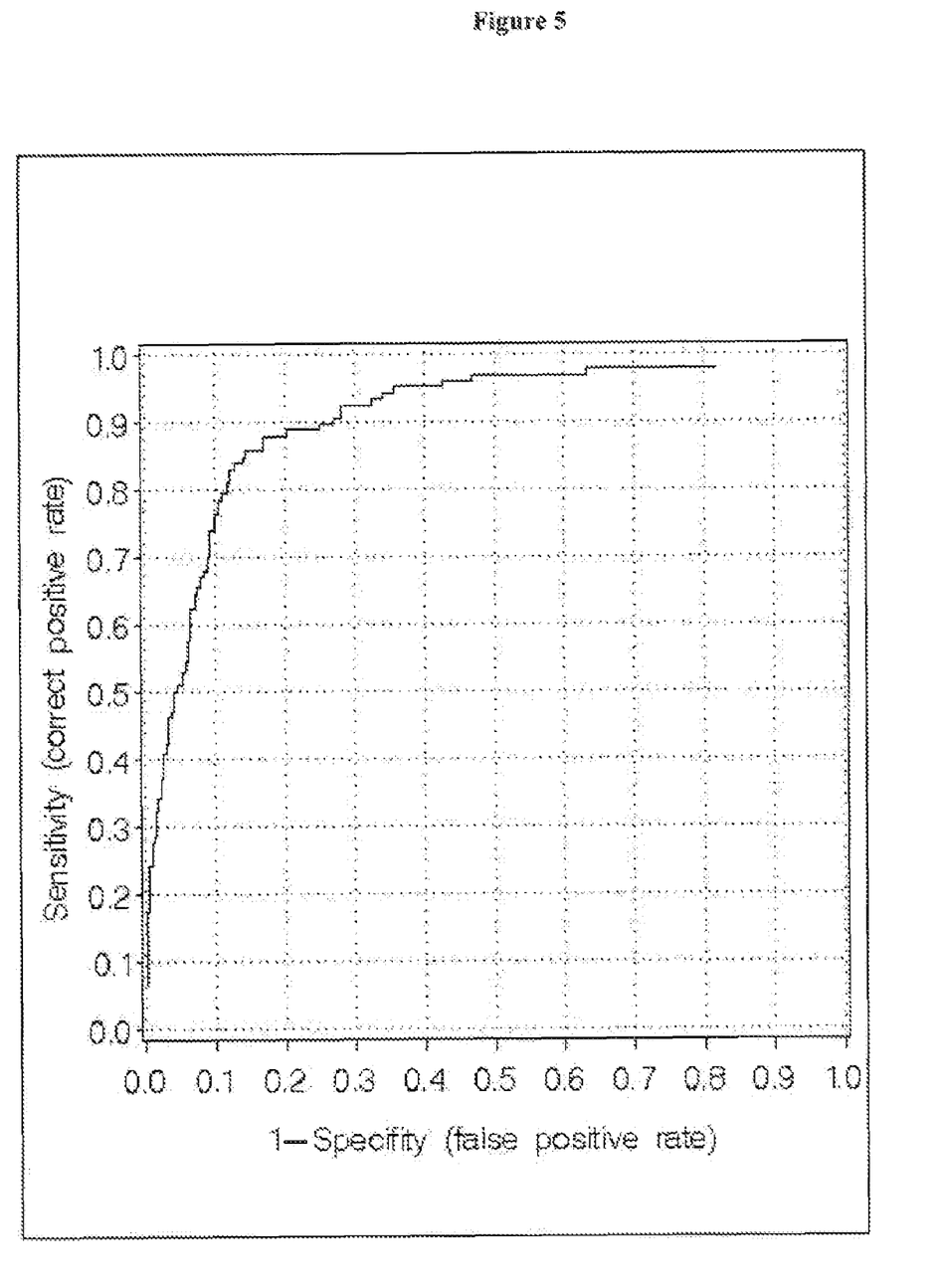
FIG. 5 ROC-analysis of patients diagnosed with CRC versus healthy controls and disease controls using the combination of log CYFRA 21-1, log NSE, log ASC and log NNMT.

The most interesting ROC-curves for the markers and marker combinations, respectively, of Tables 4 and 5, respectively, are shown in FIGS. 1 to 5.

Example 4

Analysis of a 2$^{nd}$ Study Population

In a similar fashion as described in Example 3 RDA was performed using a marker panel comprising CYFRA 21-1, OPN, FERR, NNMT, NSE and MASP.

TABLE 6

2$^{nd}$ study population: CRC samples and corresponding UICC classification

| Stages according to UICC | Number of samples |
|---|---|
| UICC 0 | 8 |
| UICC I | 41 |
| UICC II | 53 |
| UICC III | 67 |
| UICCI-III (unclassified, non-IV stages) | 13 |
| UICC IV | 61 |
| without staging | 11 |
| total number of CRC samples | 254 |

The second study population comprised serum samples from 254 patients diagnosed with CRC (see Table 6) and 391 control samples. These were split into a training set and a test set. The analysis was based on a training set of 128 CRC samples and 195 controls. Of the controls 16 were from individuals without any gastro-intestinal disease, 50 from individuals with hemorrhoids, 5 from patients with other bowel diseases; 63 controls came from individuals with diverticulosis, 61 from healthy blood donors. The test set consisted of 126 CRC samples and 196 controls. Of the controls 20 were from individuals without any gastro-intestinal disease, 43 from individuals with hemorrhoids, 8 from patients with other bowel diseases; 65 controls came from individuals with diverticulosis, 60 from healthy blood donors.

The data presented in Tables 7 and 8 indicate that with an underlying specificity of 90% the markers CYFRA 21-1, OPN and NNMT each provide a sensitivity between 30% and 40%. A combination of CYFRA 21-1 and OPN substantially increases sensitivity. In order to assess, whether addition of a third marker enhances detection performance, a third marker was included. Among several tested combinations CYFRA 21-1, OPN and FERR provide a particular advantage in that sensitivity is again increased substantially over the combination of CYFRA 21-1 and OPN only.

TABLE 7

Classification, results on the training set of patients diagnosed with CRC versus healthy controls and disease contrls

| | | | | Cross validation (5-fold) | | Classification of test set | |
|---|---|---|---|---|---|---|---|
| No of Markers | Marker or marker panel | Method (RDA) | Cut-off | Sensitivity | Specificity | Correct pos. (sensitivity) | Correct neg. (specificity) |
| 1 | log CYFRA | $\lambda = 0.75$, $\gamma = 0$ | 0.6 | 39.1% | 90.1% | 37.3% | 92.3% |
| 1 | log OPN | $\lambda = 0.5$, $\gamma = 0$ | −0.4 | 34.1% | 90.9% | 30.2% | 92.3% |
| 1 | log FERR | $\lambda = 0.75$, $\gamma = 0$ | 0.1 | 12.5% | 91.7% | 19% | 92.9% |
| 1 | log ASC | $\lambda = 0$, $\gamma = 0$ | −0.2 | 24.4% | 90.1% | 30.2% | 85.7% |
| 1 | log NNMT | $\lambda = 0.5$, $\gamma = 0$ | −0.4 | 36.2% | 90.4% | 31% | 90.3% |
| 1 | log NSE | $\lambda = 0.5$, $\gamma = 0$ | 0.6 | 15.8% | 90.8% | 18.2% | 93.9% |
| 1 | log MASP | $\lambda = 0.75$, $\gamma = 0$ | 0.1 | 23.6% | 90.9% | 19% | 91.3% |
| 2 | log CYFRA log OPN | $\lambda = 1$ $\gamma = 0$ | 0.2 | 45.3% | 90.6% | 45.2% | 92.3% |

TABLE 8

Classification results on the training set of patients diagnosed with CRC versus heathy controls and disease controls

| | | | | Cross validation (5-fold) | | Classification of test set | |
|---|---|---|---|---|---|---|---|
| No of Markers | Marker or marker panel | Method (RDA) | Cut-off | Sensitivity | Specificity | Correct pos. (sensitivity) | Correct neg (specificity) |
| 1 | log CYFRA | $\lambda = 0.75$, $\gamma = 0$ | 0.6 | 39.1% | 90.1% | 37.3% [28.8, 46.4] | 92.3% [87.9, 95.7] |
| 2 | log CYFRA log OPN | $\lambda = 1$, $\gamma = 0$ | 0.2 | 45.3% | 90.6% | 45.2% [36.4, 54.4] | 92.3% [87.9, 95.7] |
| 3 | log CYFRA log OPN log FERR | $\lambda = 1$ $\gamma = 0$ | 0 | 52.7% | 90.1% | 53.2% [44.1, 62.1] | 88.3% [83.3, 92.3] |

TABLE 8-continued

Classification results on the training set of patients diagnosed with CRC versus heathy controls and disease controls

| No of Markers | Marker or marker panel | Method (RDA) | Cut-off | Cross validation (5-fold) | | Classification of test set | |
|---|---|---|---|---|---|---|---|
| | | | | Sensitivity | Specificity | Correct pos. (sensitivity) | Correct neg (specificity) |
| 3 | log CYFPA log ASC log OPN | λ = 0.75, γ = 0 | 0.3 | 40.8% | 90.6% | 42.9% [34.1, 52] | 90.8% [86.2, 94.6] |
| 3 | log CYFRA log NNMT log OPN | λ = 1 γ = 0 | 0 | 45.9% | 91.4% | 42.1% [33.3, 51.2] | 91.3% [86.7, 95] |
| 3 | log CYFRA log NSE log OPN | λ = 1 γ = 0 | −0.4 | 42.8% | 90.7% | 41.3% [32.6, 50.4] | 93.9% [89.8, 96.9] |
| 3 | log CYFRA log MASP log OPN | λ = 1 γ = 0 | 0.1 | 43.6% | 90.6% | 41.3% [32.6, 50.4] | 93.9% [89.8, 96.9] |

What is claimed is:

1. A method for assessing colorectal cancer in a sample from a patient wherein the sample is a bodily fluid sample selected from the group consisting of blood, serum, plasma, urine, saliva, and synovial fluid, the method comprising the steps of:
   measuring in said sample a concentration of a fragment of cytokeratin 19 (CYFRA 21-1) and a concentration of at least one low sensitivity marker for colorectal cancer,
   combining the concentrations to form a combined marker concentration, and
   correlating the combined marker concentration to the diagnosis of colorectal cancer.

2. The method of claim 1 wherein the low sensitivity marker is selected from the group consisting of neuron-specific enolase (NSE), apoptosis-associated speck-like protein containing a caspase-associated recruitment domain (ASC), nicotinamide N-methyltransferase (NNMT), carbohydrate antigen 19-9 (CA 19-9), carbohydrate antigen 72-4 (CA 72-4), carcinoembryonic antigen (CEA), maspin precursor (MASP), osteopontin (OPN), and ferritin (FERR).

3. The method of claim 2 wherein said marker is NSE.

* * * * *